United States Patent [19]

Tietze et al.

[11] Patent Number: 4,524,202

[45] Date of Patent: Jun. 18, 1985

[54] PROCESS FOR THE PREPARATION OF 1,1'-DIACETALS

[75] Inventors: Lutz-Friedjan Tietze, Goettingen; Roland Fischer, Noertenhardenberg, both of Fed. Rep. of Germany

[73] Assignee: Bayer Aktiengesellschaft, Leverkusen, Fed. Rep. of Germany

[21] Appl. No.: 391,655

[22] Filed: Jun. 24, 1982

[30] Foreign Application Priority Data

Jul. 17, 1981 [DE] Fed. Rep. of Germany ....... 3128271

[51] Int. Cl.³ .............................................. C07H 1/00
[52] U.S. Cl. .................................. 536/18.5; 536/18.6; 536/121; 536/124; 568/591; 568/592; 568/603
[58] Field of Search ...................... 536/4.1, 18.5, 18.6, 536/121, 124; 568/591, 592, 603

[56] References Cited

U.S. PATENT DOCUMENTS

| | | | |
|---|---|---|---|
| 3,632,860 | 1/1972 | Marbet | 568/591 |
| 4,096,321 | 6/1978 | Weigele et al. | 536/121 |
| 4,272,526 | 6/1981 | Simpkins et al. | 536/115 |
| 4,280,011 | 7/1981 | DeSimone | 568/603 |
| 4,374,831 | 2/1983 | Joseph et al. | 536/4.1 |
| 4,374,832 | 2/1983 | Joseph et al. | 536/4.1 |

*Primary Examiner*—Johnnie R. Brown
*Attorney, Agent, or Firm*—Sprung, Horn, Kramer & Woods

[57] ABSTRACT

The invention relates to a process for the synthesis of 1,1'-diacetals, which method is also suitable for the stereoselective synthesis of glycosides with the 1,1'-diacetal structure. The process involves reacting a silyl compound of formula (II) with an acetal of formula (III) in the presence of a catalyst of formula (IV) or (V) in a suitable solvent.

8 Claims, No Drawings

PROCESS FOR THE PREPARATION OF 1,1'-DIACETALS

The present invention relates to an unobvious process for the production of certain 1,1'-diacetals.

The stereoselective formation of glycosides is one of the most demanding synthetic problems in the chemistry of natural products (G. Wulff and G. Röhle, Angew. Chem. 86, 173 (1974); Angew. Chem. Int. Ed. Engl. 13, 157 (1974)). In this respect, the synthesis of glycosides with the 1,1'-diacetal structure, as present in the 1,1-linked disaccharides or iridoid-glycosides (L.-F. Tietze and U. Niemeyer, Chem. Ber. 111, 2,423 (1978); L.-F. Tietze, U. Niemeyer, P. Marx, K.-H. Glüsenkamp and L. Schwenen, Tetrahedron 36, 735 (1980); and L.-F. Tietze, U. Niemeyer, P. Marx and K.-H. Glüsenkamp, Tetrahedron 36, 1,231 (1980)), is particularly difficult.

A surprisingly simple method for the synthesis of certain 1,1'-diacetals has now been found, which method is suitable, inter alia, also for the stereoselective synthesis of glycosides with the 1,1'-diacetal structure.

According to the present invention, there is provided a process for the production of a 1,1'-diacetal of the formula

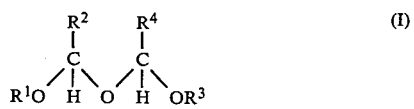

in which $R^1$ and $R^2$, which are identical or different, represent an optionally substituted aliphatic saturated or unsaturated hydrocarbon radical, it being possible for $R^1$ and $R^2$ to be bonded to each other, $R^3$ represents an optionally substituted alkyl radical and $R^4$ represents an optionally substituted O-alkyl radical or an optionally substituted, saturated or unsaturated, aliphatic radical, in which a silyl compound of the formula

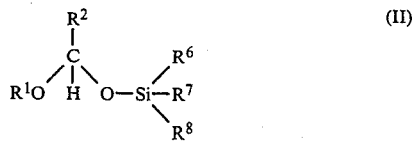

in which $R^1$ and $R^2$ have the abovementioned meanings and $R^6$, $R^7$ and $R^8$, are identical or different and represent an optionally substituted alkyl radical, is reacted with an acetal of the formula

in which $R^3$ and $R^4$ have the abovementioned meanings, and $R^5$ represents an optionally substituted alkyl or phenyl radical, in the presence of a catalyst of the formula

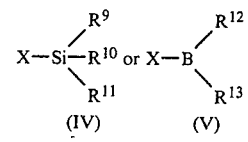

in which $R^9$, $R^{10}$, $R^{11}$, $R^{12}$ and $R^{13}$, which are identical or different, represent an alkyl radical having 1 to 8 carbon atoms, and X represents $FSO_3$, $CF_3CO_2$, $ClO_4$, $BF_4$, $CH_3SO_3$ or $CF_3(CF_2)_n-SO_3$ (in which n is 0, 1, 2, 3 or 4), in a suitable solvent.

Silyl compounds of formula (II), used as starting materials are in themselves known (see inter alia, L. Birkofer, A. Ritter and F. Bentz, Chem. Ber. 97, 2,196 (1964); and A. Klemmer, E. Buhe and R. Kutz, Liebigs Ann. Chem. 739, 185 (1970)).

Preferred 1,1'-diacetals of formula (I) produced by the process of the present invention are those, in which $R^1$ and $R^2$, which are identical or different, denote an aliphatic, saturated or unsaturated hydrocarbon radical having 1 to 6 carbon atoms (optionally substituted by 1 to 6, especially 1, 2 or 3 substituents preferably selected from (protected) OH, O-alkyl, preferably having 1 to 4 carbon atoms, alkoxycarbonyl, preferably having 1 to 4 carbon atoms in the alkoxy portion and phenyl), or $R^1$ and $R^2$ together represent an alkylene radical preferably having 3 or 4 carbon atoms, which can be optionally substituted as indicated immediately above, $R^3$ denotes an optionally substituted alkyl radical having 1 to 6 carbon atoms, and $R^4$ denotes an optionally substituted O-alkyl radical having 1 to 6 carbon atoms, or an optionally substituted, saturated or unsaturated, aliphatic radical having 1 to 6 carbon atoms (preferred substituents for $R^3$ and $R^4$ being 1 to 6, especially 1, 2 or 3 substituents, preferably selected from those mentioned for $R^1$ and $R^2$, and halogen).

Preferred starting materials of formula (III) are those, in which $R^3$ and $R^4$ have those meanings given above for those radicals, and $R^5$ denotes an optionally substituted alkyl radical having 1 to 10 carbon atoms, preferably 1 to 6 carbon atoms, or a phenyl radical optionally substituted by halogen, nitro or O-alkyl (preferably having 1 to 4 carbon atoms).

Preferred starting materials of formula (II) are those, in which $R^1$ and $R^2$ have those meanings given above for these radicals, and $R^6$, $R^7$ and $R^8$, which are identical or different denote an alkyl radical having 1 to 8 (particularly 1–4) carbon atoms, especially a methyl radical.

Preferred catalysts of formula (IV) or (V) are those in which $R^9$, $R^{10}$, $R^{11}$, or $R^{12}$ and $R^{13}$, are identical or different and denote an alkyl radical having 1 to 8 (particularly 1 to 4) carbon atoms, especially a methyl radical and X has the abovementioned meaning, especially $CF_3SO_3$.

Particularly preferably all of the radicals $R^6$, $R^7$, $R^8$, $R^9$, $R^{10}$, $R^{11}$, $R^{12}$ and $R^{13}$ denote methyl radicals.

In a particularly preferred mode of the invention the compound (II) represents a compound of the formula (VI)

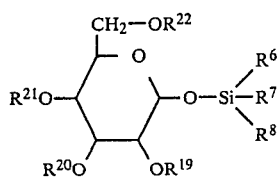

wherein $R^{19}$–$R^{22}$ are the same or different and represent a protective group for OH-group.

Most preferably, the radicals $OR^{19}$–$OR^{21}$ and the radical $CH_2$—$OR^{22}$ together with the basic ring system are in a glucose-configuration.

The customary protective groups, such as acetyl, benzyloxycarbonyl, benzyl or trityl, are suitable OH protective groups on the abovementioned (protected) OH substituent.

In carrying out the reaction the silyl compound of formula (II) is preferably reacted with equimolar amounts or an excess of the compound of formula (III). Preferably about 1/10 equivalent of the catalyst of formula (IV) or (V) relative to the silyl compound of formula (II) is used.

Preferred solvents for the reaction according to the present invention are $CH_2Cl_2$, $CHCl_3$, acetonitrile, diethyl ether or tetrahydrofuran.

The reaction is carried out within a wide temperature range, preferably at a temperature between $-80°$ C. and $100°$ C. If the reaction is carried out in a temperature range between $-80°$ and $-40°$ C., a compound of formula (I) is formed with retention of the configuration at C-1, whereas at $0°$ to $100°$ C. inversion occurs.

EXAMPLES

The equations which follow illustrate the reactions tabulated below. The description and the tables refer to the numbers below the formulae. Where a formula does not define a single compound, the individual compounds are referred to by the number and a lower case letter. The identity of those individual compounds are indicated in Table 1.

Above and hereinafter, the abbreviations used have the following meanings:
Me = Methyl
Ac = Acetyl
Bn = Benzyl
Ph = Phenyl
$R^{17}$, $R^{18}$

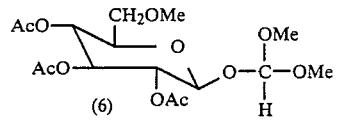

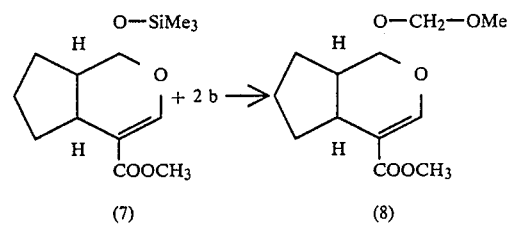

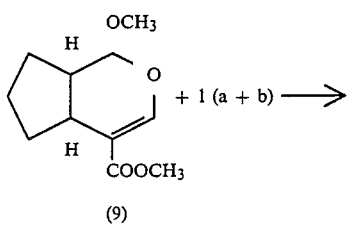

|  |  | Product |
|---|---|---|
| Reactant 1 | Reactant 2 | (obtain from Reactants with indicated specific radical meanings) |

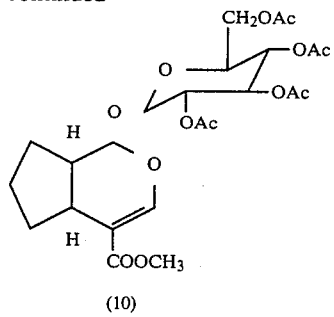

(10)

The acetals (2) which are used for the preparation of the products (3) and (4) can be replaced by the respective aldehyds (11) and methyl-trimethylsilyl ether (12) (c.f. T. Tsunoda et al., Tetrahedron Letters 1980, 1357).

The yields of compounds (3) and (4) so obtained are comparable or better than those listed in Table 2.

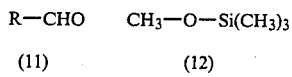

Examples for R are $CH_2-C_6H_5$, $n-C_3H_7$, $CH_2OCH_3$ and $CH_2Cl$.

GENERAL PROCEDURE

To a solution of 0,25 mmol silylcompound (1), 0,25 mmol aldehyde (11) and 0,35 mmol methyl-trimethylethyl-silyl ether (12) in 2 ml dry $CH_2Cl_2$ 0,2 ml of a 0,1 molar solution of trimethylsilyl-trifluoromethan sulfonate in $CH_2Cl_2$ are added at $-70°$ C. and under inert atmosphere. The mixture is stirred for 20–60 hours at this temperature. The reaction can be surveyed by DC with silicagel and hexan/ethyl acetate 1:1 (V/V) as running agent.

It has further been found that a significant increase of the reaction velocity can be achieved in the acetalisation, if about 0,5 mol equivalents of aceton based on e.g. trimethylsilylglucose are added.

| Reactant 1 | $R^{16}$ | $R^{14}$ | $R^{15}$ |
|---|---|---|---|
| 1a | Ac | OSiMe$_3$ | H |
| 1b | Ac | H | OSiMe$_3$ |
| 1c | Bn | OSiMe$_3$ | H |
| 1d | Bn | H | OSiMe$_3$ |
| Reactant 2 | | $R^5$ | $R^4$ |
| 2a | | Me | H |
| 2b | | Ph | H |
| 2c | | Me | CH$_2$Ph |
| 2d | | Me | n-C$_3$H$_7$ |
| 2e | | Me | CH$_2$—CH(OMe)$_2$ |
| 2f | | Me | CH$_2$—OMe |
| 2g | | H | CH$_2$Cl |
| 2h | | Me | CH$_2$Br |
| 2i | | Me | OMe |
| Product | | | $R^4$ |
| 3a | 4a | | H |
| 3b | 4b | | CH$_2$Ph |
| 3c | 4c | | n-C$_3$H$_7$ |
| 3d | 4d | | CH$_2$—CH(OMe)$_2$ |
| 3e | 4e | | CH$_2$—OMe |
| 3f | 4f | | CH$_2$Cl |
| 3g | 4g | | CH$_2$Br |
| 3h | | | OMe |
| Product | $R^{17}$ | | $R^{18}$ |
| 5a | H | | OCH$_2$—OMe |
| 5b | OCH$_2$—OMe | | H |

The reactions were carried out according to the following instructions.

(A) 0.2 ml of a 0.1 molar solution of trimethylsilyl trifluoromethanesulphonate in dichloromethane is added to a solution of 0.25 mmol of the silyl compound (1 or 7) and 0.50 mmol of the acetal (2) in 3 ml of anhydrous dichloromethane at $-70°$ C., under an inert gas atmosphere, and the mixture is stirred at this temperature for from 20 to 60 hours. The course of the reaction can be followed by thin layer chromatography on silica gel (mobile phase: hexane/ethyl acetate 1:1).

(B) 0.1 ml of a 0.1 molar solution of trimethylsilyl trifluoromethanesulphonate in dichloromethane is added to a solution of 0.25 mmol of the silyl compound (1) and 0.50 mmol of the acetal (2) in 5 ml of anhydrous dichloromethane at $0°$ C., under an inert gas atmosphere, and the mixture is stirred at this temperature for from 4 to 16 hours. The course of the reaction can be followed by thin layer chromatography on silica gel (mobile phase: hexane/ethyl acetate 1:1).

(C) 0.2 ml of a 0.1 molar solution of trimethylsilyl trifluoromethanesulphonate in dichloromethane is added to a solution of 105 mg (0.25 mmol) of the silyl compound (1a) and 53.0 mg (0.50 mmol) of methyl orthoformate (2i) in 3 ml of anhydrous dichloromethane at $-30°$ C., under an inert gas atmosphere, and the mixture is stirred at this temperature for approx. 40 hours. After working up, 70 mg of a mixture of (3h) and (6) are obtained.

(D) 42.4 mg (0.2 mmol) of (9) are reacted with 84.0 mg (0.2 mmol) of (1) ($\alpha,\beta$ mixture), according to method C (reaction time 6 days). 93.8 mg (89%) of the isomeric glucoside (10) are obtained. The product is identified by comparison with original substances.

WORKING-UP

To work up the reaction mixture, 0.1 ml of triethylamine are added and the mixture is washed with saturated NaHCO$_3$ solution and NaCl solution and dried over Na$_2$SO$_4$/Na$_2$CO$_3$ (1:1). After the solvent has been evaporated off in vacuo, the product obtained consists almost of a single substance, and can be chromatographed over silica gel for further purification.

(Z) To determine the configuration at C-1, the tetraacetates (3 and 4) were converted solvolytically, using methanol/sodium methanolate, into the free glucosides.

Table 2 below shows the reactants employed, the procedure, the yields and the products and their characterisation.

TABLE 2

| Reactants | Method | Product | Yield (%) | $^1$H—NMR ($\delta$ = ppm) | IR | Analysis Calculated | Found |
|---|---|---|---|---|---|---|---|
| 1a + 2a | A | 1-O—(1'-methoxy- | 75 | (100 MHz, CDCl$_3$): | (KBr): | C: 48.98 | 49.09 |
| 1a + 2b | A | methyl)-2,3,4,6- | 88 | 1.97 (s, 3H, CH$_3$), | 2990, 2960 | H: 6.17 | 6.19 |
| | | tetra-O—acetyl- | | 2.01 (s, 6H, CH$_3$), | 2920 (CH), | C$_{16}$H$_{24}$O$_{11}$ | |

TABLE 2-continued

| Reactants | Method | Product | Yield (%) | $^1$H—NMR ($\delta$ = ppm) | IR | Analysis Calculated | Found |
|---|---|---|---|---|---|---|---|
| | | β-D-glucopyranose (3a) | | 2.05 (s, 3H, CH$_3$), 3.35 (s, 3H, OCH$_3$), 3.69 (m, 1H, 5-H), 4.05 (d, d J = 12 Hz and 2.5 Hz, 1H, 6-H), 4.28 (d, d J = 12 Hz and 4.5 Hz, 1H, 6-H), 4.50–5.13 (m, 6H, 1-H, 1-H, 2-H, 3-H, 4-H) | 2840 (acetal) 1760, 1745 (CO) | (392.36) | |
| | Z | 1-O—(1'-methoxymethyl)-β-D-glucopyranose | | (80 MHz, D$_6$-acetone/D$_2$): 3.20–4.00 (m, 6H, 2-H, 3-H, 4-H, 5-H, 6-H), 3.46 (s, 3H, OCH$_3$), 4.45 (s, 4H, OH), 4.58 (d, J = 7.5 Hz, 1H, 1-H), 4.73 (d, J = 6.5 Hz, 1H, 1'-H) 5.02 (d, J = 6.5 Hz, 1H, 1'-H) | | | |
| 1b + 2b | A | 1-O—(1'-methoxymethyl)-2,3,4,6-tetra-O—acetyl-α-D-glucopyranose (4a) | 87 | (100 MHz, CDCl$_3$): 1.99 (s, 3H, CH$_3$), 2.01 (s, 3H, CH$_3$), 2.04 (s, 3H, CH$_3$), 2.07 (s, 3H, CH$_3$), 3.38 (s, 3H, OCH$_3$), 3.99–4.35 (m, 3H, 5-H, 6-H), 4.54–5.60 (m, 6H, 1'-H, 1-H, 2-H, 3-H, 4-H) | | | |
| | Z | 1-O—(1'-methoxymethyl)-α-D-glucopyranose | | (80 MHz, D$_6$-acetone/D$_2$): 3.50–4.00 (m, 6H, 2-H, 3-H, 4-H, 5-H, 6-H), 3.55 (s, 3H, OCH$_3$), 4.20 (s, 4H, OH), 4.75 (d, J = 6.5 Hz, 1H, 1'-H), 5.03 (d, J = 6.5 Hz, 1H, 1'-H), 5.17 (d, J = 3.75 Hz, 1H, 1-H) | | | |
| 1a + 2c | A | 1-O—(1'-methoxy-2'-phenyl-ethyl-2,3,4,6-tetra-O—acetyl-β-D-glucopyranose (3b) | 84 | (100 MHz, CDCl$_3$): 2.01 (s, 3H, CH$_3$), 2.04 (s, 3H, CH$_3$), 2.06 (s, 3H, CH$_3$), 2.08 (s, 3H, CH$_3$), 2.90–3.03 (m, 2H, 2'-H), 2.35 and 2.40 (s, 3H, OCH$_3$), 3.60–3.85 (m, 1H, 5-H), 4.06–4.33 (m, 2H, 6-H), 4.71–5.19 (m, 5H, 1'-H, 1-H, 2-H, 3-H, 4-H), 7.27 (m, 5H, C$_6$H$_5$) | (KBr): 3030 (CH aromatic) 2980, 2960 2940 (CH aliphatic) 2840 (acetal) 1745 (CO) | | |
| | Z | 1-O-(1'-methoxy-2'-phenyl-ethyl)-β-D-glucopyranose | | (100 MHz, D$_6$-acetone/D$_2$O): 2.95–3.08 (m, 2H, 2'-H), 3.32–3.56 (m, 4H, 2-H, 3-H, 4-H, 5-H), 3.37 and 3.39 (2s, 3H, OCH$_3$), 3.60–3.98 (m, 2H, 6-H), 4.29 (s, 4H, OH), 4.57 and 4.67 (2d, J = 7.5 Hz, 1H, 1-H), 4.87 and 5.03 (2d, d, J = 7 Hz and 4 Hz, 1H, 1'-H), 7.27 (m, 5H, C$_6$H$_5$) | | C: 57.32 H: 7.06 C$_{15}$H$_{22}$O$_7$ (314.33) | 57.41 7.08 |
| 1a + 2c | B | 1-O—(1'-methoxy-2'-phenyl-ethyl)-2,3,4,6-tetra-O—acetyl-α-D-glucopyranose (4b) | 72 | (80 MHz, CDCl$_3$): 2.00 (s, 3H, CH$_3$), 2.02 (s, 3H, CH$_3$), 2.04 (s, 3H, CH$_3$), 2.07 (s, 3H, CH$_3$), 2.87–3.07 (m, 2H, 2'-H), 3.35 and 3.37 2s, 3H, OCH$_3$), 3.55 (d, d, J = 12.5 Hz and 2.5 Hz, 1H, 6-H), 3.87 (d, d, j = 12.5 Hz and 3.75 Hz, 1H, 6-H), 4.02–4.25 (m, 1H, 5-H), 4.6–5.63 (m, 5H, 1'-H, 1-H, 2-H, 3-H, 4-H), 7.25 | | | |

TABLE 2-continued

| Reactants | Method | Product | Yield (%) | $^1$H—NMR ($\delta$ = ppm) | IR | Analysis Calculated | Found |
|---|---|---|---|---|---|---|---|
| | Z | 1-O—(1'-methoxy-2'-phenyl-ethyl)-α-D-glucopyranose | | (m, 5H, C$_6$H$_5$) (80 MHz, D$_6$-acetone/D$_2$O): 2.98 (d, J = 5.5 Hz, 2H, 2'-H), 3.1-3.8 (m, 6H, 2-H, 3-H, 4-H, 5-H, 6-H), 3.37 and 3.39 (2s, 3H, OCH$_3$), 3.89 (s, 4H, OH), 4.91 (t, J = 5.5 Hz, 1H, 1'-H), 5.09 (d, J = 3.75 Hz, 1H, 1-H), 7.25 (m, 5H, C$_6$H$_5$) | | | |
| 1a + 2d | A | 1-O—(1'-methoxy-butyl)-2,3,4,6-tetra-O—acetyl-β-D-glucopyranose (3c) | 78 | (100 MHz, CDCl$_3$): 0.95 (t, J = 7 Hz, 3H, 4'-H) 1.22-1.82 (m, 4H, 2'-H, 3'-H), 2.01 (s, 3H, CH$_3$), 2.04 (s, 6H, CH$_3$), 2.08 (s, 3H, CH$_3$), 3.31 and 3.37 (2s, 3H, OCH$_3$), 3.62-3.80 (m, 1H, 5-H), 4.08-4.34 (m, 2H, 6-H), 4.49-5.34 (m, 5H, 1'-H, 1-H, 2-H, 3-H, 4-H) | (Film) 2960, 2940 2880 (CH) 2840 (acetal) 1745 (CO) | C: 52.53 H: 6.96 C$_{19}$H$_{30}$O$_{11}$ (434.44) | 52.60 7.01 |
| | Z | 1-O—(1'-methoxy-butyl)-β-D-glucopyranose | | (100 MHz, D$_6$-acetone/D$_2$O): 0.89 (t, J = 7.0 Hz, 3H, 4'-H), 1.14-1.80 (m, 4H, 2'-H, 3'-H), 3.18-3.54 (m, 4H, 2-H, 3-H, 4-H, 5-H), 3.38 and 3.42 (2s, 3H, OCH$_3$), 3.66 (d, d, J = 12.5 Hz and 2.5 Hz, 1H, 6-H), 3.86 (d, d, J = 12.0 Hz and 2.0 Hz, 1H, 6-H), 4.05 (s, 4H, OH), 4.47 and 4.59 (2d, J = 7.5 Hz, 1H, 1-H), 4.64 and 4.83 (2t, J = 5.0 Hz, 1H, 1'-H) | | | |
| 1a + 2d | B | 1-O—(1'-methoxy-butyl)-2,3,4,6-tetra-O—acetyl-α-D-glucopyranose (4c) | 57 | (60 MHz, CDCl$_3$): 0.80-1.60 (m, 7H, 2'-H, 3'-H, 4'-H), 1.92 (s, 3H, CH$_3$), 1.94 (s, 3H, CH$_3$), 1.96 (s, 3H, CH$_3$), 2.00 (s, 3H, CH$_3$), 3.23 and 3.34 (2s, 3H, OCH$_3$), 3.89-4.26 (m, 3H, 5-H, 6-H), 4.45-5.60 (m, 5H, 1'-H, 1-H, 2-H, 3-H, 4-H) | | | |
| | Z | 1-O—(1'-methoxy-butyl)-α-D-glucopyranose | | (80 MHz, D$_6$-acetone/D$_2$O): 0.82-1.82 (m, 7H, 2'-H, 3'-H, 4'-H), 3.36 and 3.42 (2s, 3H, OCH$_3$), 3.28-3.85 (m, 6H, 2-H, 3-H, 4-H, 5-H, 6-H), 4.01 (s, 4H, OH), 4.53-4.90 (m, 1H, 1'-H), 5.02 and 5.08 (2d, J = 3.75 Hz, 1H, 1-H) | | | |
| 1a + 2e | A | 1-O—(1',3',3'-trimethoxypropyl)-2,3,4,6-tetra-O—acetyl-β-D-glucopyranose | 79 | (60 MHz, CDCl$_3$): 2.00 (s, 3H, CH$_3$), 2.02 (s, 6H, CH$_3$), 2.04 (s, 3H, CH$_3$), 1.83-2.04 (m, 2H, 2'-H), 3.29 and 3.36 (2s, 3H, OCH$_3$), 3.30 (s, 6H, OCH$_3$), 3.55-3.86 (m, 1H, 5-H), 3.92-4.28 (m, 2H, 6-H), 4.34-5.18 (m, 6H, 1-H, | (Film): 2950, 2920 (CH) 2850 (acetal) 1750 (CO) | | |

TABLE 2-continued

| Reactants | Method | Product | Yield (%) | $^1$H—NMR ($\delta$ = ppm) | IR | Analysis Calculated | Found |
|---|---|---|---|---|---|---|---|
| | Z | 1-O—(1',3',3'-trimethoxypropyl)-$\beta$-D-glucopyranose | | 1'-H, 2-H, 3-H, 3'-H, 4-H) (80 MHz, D$_6$-acetone/D$_2$O): 1.89–2.14 (m, 2H, 2'-H), 3.33 (s, 6H, OCH$_3$), 3.43 and 3.45 (2s, 3H, OCH$_3$), 3.16–3.95 (m, 6H, 2-H, 3-H, 4-H, 5-H, 6-H), 4.12 (s, 4H, OH), 4.63 and 4.71 (2d, J = 7.5 Hz, 1H, 1-H), below this 4.45–4.93 (m, 2H, 1'-H, 3'-H) | | | |
| 1a + 2e | B | 1-O—(1',3',3'-trimethoxypropyl)-2,3,4,6-tetra-O-acetyl-$\alpha$-D-glucopyranose (4d) | 79 | (100 MHz, CDCl$_3$): 1.92–2.14 (m, 2H, 2'-H), 1.98 (s, 3H, CH$_3$), 2.00 (s, 3H, CH$_3$), 2.02 (s, 3H, CH$_3$), 2.06 (s, 3H, CH$_3$), 3.26 and 3.38 (2s, 3H, OCH$_3$), 3.30 (s, 6H, OCH$_3$), 3.99–4.26 (m, 3H, 5-H, 6H), 4.39–5.57 (m, 6H, 1-H, 1'-H, 2-H, 3-H, 3'-H, 4-H) | | | |
| | Z | 1-O—(1',3',3'-trimethoxypropyl)-$\alpha$-D-glucopyranose | | (100 MHz, D$_6$-acetone/D$_2$O): 1.92–2.17 (m, 2H, 2'-H), 3.32 (s, 6H, OCH$_3$), 3.38 and 3.42 (2s, 3H, OCH$_3$), below this to 3.82 (m, 6H, 2-H, 3-H, 4-H, 5-H, 6-H), 4.26 (s, 4H, OH), 4.49–4.88 (m, 2H, 1'-H, 3'-H), 5.02 and 5.12 (2d, J = 3.75 Hz, 1H, 1-H) | | | |
| 1a + 2f | A | 1-O—(1',2'-dimethoxyethyl)-2,3,4,6-tetra-O—acetyl-$\beta$-D-glucopyranose (3e) | 77 | (60 MHz, CDCl$_3$): 2.00 (s, 3H, CH$_3$), 2.02 (s, 3H, CH$_3$), 2.03 (s, 3H, CH$_3$), 2.04 (s, 3H, CH$_3$), 3.33–3.47 (m, 8H, 2'-H, OCH$_3$), 3.56–3.89 (m, 1H, 5-H), 4.07–4.36 (m, 2H, 6-H), 4.70–5.21 (m, 5H, 1-H, 1'-H, 2-H, 3-H, 4-H) | | | |
| | Z | 1-O—(1',2'-dimethoxyethyl)-$\beta$-D-glucopyranose | | (100 MHz, D$_6$-acetone/D$_2$O): 3.21–3.95 (m, 8H, 2-H, 2'-H, 3-H, 4-H, 5-H, 6-H), 3.35 (s, 3H, OCH$_3$), 3.45 and 3.47 (2s, 3H, OCH$_3$), 4.18 (s, 4H, OH), 4.57 and 4.67 (2d, J = 7.5 Hz, 1H, 1-H), 4.79 and 4.94 (2t, J = 5.5 Hz, 1H, 1'-H) | | | |
| 1a + 2f | B | 1-O—(1',2'-dimethoxyethyl)-2,3,4,6-tetra-O—acetyl-$\alpha$-D-glucopyranose (4e) | 84 | (100 MHz, CDCl$_3$): 2.02 (s, 3H, CH$_3$), 2.04 (s, 3H, CH$_3$), 2.06 (s, 3H, CH$_3$), 2.10 (s, 3H, CH$_3$), 3.36, 3.40 and 3.47 (3s, 6H, OCH$_3$), 3.30–3.52 (m, 2H, 2'-H), 3.98–4.37 (m, 3H, 5-H, 6-H), 4.64–5.64 (m, 5H, 1-H, 1$\alpha$-H, 2-H, 3-H, 4-H) | (Film): 3020, 2940 (CH) 2850 (acetal) 1750 (CO) | | |
| | Z | 1-O—(1',2'-dimethoxyethyl)-$\alpha$-D-glucopyranose | | (80 MHz, D$_6$acetone/D$_2$O): 3.40–3.78 (m, 8H, 2'-H, 2-H, 3-H, 4-H, 5-H, 6-H), 3.40, 3.48 and 3.53 (3s, 6H, OCH$_3$), 4.52 (s, 4H, OH), 4.72–4.96 (m, 1H, | | | |

TABLE 2-continued

| Reactants | Method | Product | Yield (%) | $^1$H—NMR ($\delta$ = ppm) | IR | Analysis Calculated | Found |
|---|---|---|---|---|---|---|---|
| | | | | 1'-H), 5.12 and 5.20 (2d, J = 3.75 Hz, 1H, 1-H) | | | |
| 1a + 2g | A | 1-O—(2'-chloro-1'-methoxyethyl)-2,3,4,6-tetra-O—acetyl-$\beta$-D-glucopyranose | 71 | (60 MHz, CDCl$_3$): 2.03 (s, 3H, CH$_3$), 2.06 (s, 6H, CH$_3$), 2.08 (s, 3H, CH$_3$), 3.45–3.98 (m, 6H, 2'-H, 5-H, OCH$_3$), 4.20–4.34 (m, 2H, 6H), 4.67–5.23 (m, 5H, 1-H, 1'-H, 2-H, 3-H, 4-H) | | | |
| | Z | 1-O—(2'-chloro-1'-methoxyethyl)-$\beta$-D-glucopyranose | | (80 MHz, D$_6$-acetone/D$_2$O): 3.40–3.95 (m, 8H, 2'-H, 2-H, 3-H, 4-H, 5-H, 6-H), 3.42 and 3.49 (2s, 3H, OCH$_3$), 3.65 (s, 4H, OH), 4.56 and 4.62 (2d, J = 7.5 Hz, 1H, 1-H), 4.82 and 4.92 (2d, d, J = 7 Hz and 3.75 Hz, 1H, 1'-H) | | | |
| 1a + 2g | B | 1-O—(2'-chloro-1'-methoxyethyl)-2,3,4,6-tetra-O—acetyl-$\alpha$-D-glucopyranose (4f) | 82 | (100 MHz, CDCl$_3$): 1.98 (s, 3H, CH$_3$), 2.01 (s, 3H, CH$_3$), 2.02 (s, 3H, CH$_3$), 2.05 (s, 3H, CH$_3$), 3.37–3.59 (m, 5H, 2'-H, OCH$_3$), 4.01–4.29 (m, 3H, 5-H, 6-H), 4.62–5.58 (m, 5H, 1-H, 1'-H, 2-H, 3-H, 4-H) | (Film): 2980, 2950 (CH) 2860 (acetal) 1750 (CO) | | |
| | Z | 1-O—(2'-chloro-1'-methoxyethyl)-$\alpha$-D-glucopyranose | | (60 MHz, D$_6$-acetone/D$_2$O): 3.33–3.86 (m, 8H, 2-H, 2'-H, 3-H, 4-H, 5-H, 6-H), 3.50 and 3.53 (2s, 3H, OCH$_3$), 4.25 (s, 4H, OH), 4.56–5.01 (m, 1H, 1'-H), 5.19 and 5.21 (2d, J = 3.75 Hz, 1H, 1-H) | | | |
| 1a + 2h | A | 1-O—(2'-bromo-1'methoxyethyl)-2,3,4,6-tetra-O—acetyl-$\beta$-D-glucopyranose (3g) | 78 | (60 MHz, CDCl$_3$): 2.02 (s, 3H, CH$_3$), 2.04 (s, 3H, CH$_3$), 2.06 (s, 3H, CH$_3$), 2.10 (s, 3H, CH$_3$), 3.36–3.50 (m, 5H, 2'-H, OCH$_3$), 3.67–3.93 (m, 1H, 5-H), 4.04–4.36 (m, 2H, 6-H), 4.73–5.26 (m, 5H, 1-H, 1'-H, 2-H, 3-H, 4-H) | | | |
| | Z | 1-O—(2'-bromo-1'-methoxyethyl)-$\beta$-D-glucopyranose | | (80 MHz, D$_6$-acetone/D$_2$O): 3.30–3.95 (m, 11H, 2'-H, OCH$_3$, 2-H, 3-H, 4-H, 5-H, 6-H), 4.11 (s, 4H, OH), 4.63 and 4.71 (2d, J = 7.5 Hz, 1H, 1-H), 4.79–5.00 (m, 1H, 1'-H) | | | |
| 1a + 2h | B | 1-O—(2'-bromo-1'-methoxyethyl)-2,3,4,6-tetra-O—acetyl-$\alpha$-D-glucopyranose (4g) | 83 | (100 MHz, CCl$_4$): 2.00 (s, 3H, CH$_3$), 2.02 (s, 3H, CH$_3$), 2.04 (s, 3H, CH$_3$), 2.07 (S,3H, CH$_3$), 3.38 and 3.46 (2s, 3H, OCH$_3$), 3.28–3.52 (m, 2H, 2'-H), 3.94–4.35 (m, 3H, 5-H, 6-H), 4.65–5.60 (m, 5H, 1-H, 1'-H, 2-H, 3-H, 4-H) | (Film): 2960 (CH) 2840 (acetal) 1745 (CO) | C: 42.08 H: 5.19 C$_{17}$H$_{25}$O$_{11}$Br (485.29) | 41.95 5.16 |
| | Z | 1-O—(2'-bromo-1'-methoxyethyl)-$\alpha$-D-glucopyranose | | (200 MHz, D$_6$-acetone/D$_2$O): 3.42–3.88 (m, 8H, 2-H, 2'-H, 3-H, 4-H, 5-H, 6-H), 3.50 and 3.54 (2s, 3H, OCH$_3$), 4.53 (s, 4H, OH), 4.89 and 4.95 (2d, d, J = 5.5 Hz and 4.0 Hz, 1H, 1'-H), 5.19 and 5.21 (2d, J = 3.75 Hz, 1H, 1-H) | | | |

TABLE 2-continued

| Reactants | Method | Product | Yield (%) | $^1$H—NMR ($\delta$ = ppm) | IR | Analysis Calculated | Found |
|---|---|---|---|---|---|---|---|
| 1a + 2i | | 1-O—(1'-dimethoxy-methyl)-6-O—methyl-2,3,4-tetra-O—acetyl-$\beta$-D-glucopyranose (6) | | Mass spectrum: MS (M/e): 363 (0.4, M$^+$—CH$_3$O), 319 (0.4, M$^+$—C$_3$H$_7$O$_2$), 303 (1.3, M$^+$—C$_3$H$_7$O$_3$), 243 (4, 303-C$_2$H$_4$O$_2$), 183 (4, 243-C$_2$H$_4$O$_2$), 141 (14, 183-C$_2$H$_2$O), 75 (98, C$_3$H$_7$O$_2$$^+$) | | | |
| 1c + 2b | A | 1-O—(1'-methoxy-methyl)-2,3,4,6-tetra-O—benzyl-$\beta$-D-glucopyranose (6a) | 89 | (60 MHz, CCl$_4$): 3.34 (s, 3H, OCH$_3$), 3.42–3.98 (m, 6H, 2-H, 3-H, 4-H, 5-H, 6-H), 4.41–4.92 (m, 11H, 1-H, 1'-H, CH$_2$), 7.04–7.33 (m, 20H, C$_6$H$_5$) | (Film): 3105, 3080 3050 (CH aromatic) 2940, 2910 2880 (CH aliphatic) | | |
| 1d + 2b | A | 1-O—(1'-methoxy-methyl)-2,3,4,6-tetra-O—benzyl-$\alpha$-D-glucopyranose (6b) | | (100 MHz, CDCl$_3$): 3.37 (s, 3H, OCH$_3$), 3.52–4.12 (m, 6H, 2-H, 3-H, 4-H, 5-H, 6-H), 4.34–5.03 (m, 10H, 1'-H, CH$_2$), 5.13 (d, J = 3.75 Hz, 1H, 1-H), 7.04–7.33 (m, 20H, C$_6$H$_5$) | 2840 (acetal) 1620, 1590, 1500 (aromatic) 740, 700 (benzene ring, monosubstituted) | | |
| 7 + 2b | A | Methyl 1-$\alpha$-O—(1'-methoxy-methyl)-1,4a$\alpha$,5,6,7a$\alpha$-hexahydrocyclopenta(c)pyran-4-carboxylate (8) | 90 | (100 MHz, CDCl$_3$): 1.18–2.32 (m, 7H, 5-H, 6-H, 7a-H), 2.76 (q, J = 8.0 Hz, 1H, 4a-H), 3.40 (s, 3H, OCH$_3$), 3.69 (s, 3H, CH$_3$), 4.59 (d, J = 6.5 Hz, 1H, 1'-H), 4.76 (d, J = 7.5 Hz, 1H, 1-H), 497 (d, J = 6.5 Hz, 1H, 1'-H), 7.39 (d, J = 1.0 Hz, 1H, 3-H) | (Film): 2960, 2900 2880 (CH) 2935 (acetal) 1610 (CO) 1630 (C═C) | 242.1154 (mass spectroscopic) C$_{12}$H$_{18}$O$_5$ | 242.1155 |

We claim:

1. Process for the production of a 1,1'-diacetal of the formula

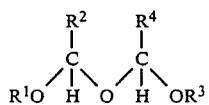  (I)

in which

R$^1$ and R$^2$ are identical or different, and each represents an aliphatic, saturated or unsaturated hydrocarbon radical having 1 to 6 carbon atoms, which is unsubstituted or substituted by 1 to 6 substituents selected from acetyl-, benzylcarbonyl-, benzyl- or trityl-protected OH, C$_1$—C$_4$—O—alkyl, C$_1$-C$_4$-alkoxycarbonyl or phenyl, or R$^1$ and R$^2$ represent C$_1$-C$_4$-alkylene which is unsubstituted or substituted by 1 to 6 substituents selected from protected OH, C$_1$-C$_4$-O-alkyl, C$_1$-C$_4$-alkoxycarbonyl or phenyl, R$^3$ represents C$_1$-C$_6$-alkyl and R$^4$ represents C$_1$-C$_6$-O-alkyl or saturated or unsaturated C$_1$-C$_6$-alkyl, which comprises reacting a silyl compound of the formula

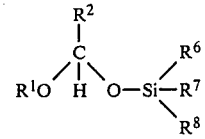  (II)

in which

R$^1$ and R$^2$ are defined as above, and in which

R$^6$, R$^7$ and R$^8$ represents C$_1$-C$_8$-alkyl, with an acetal of the formula

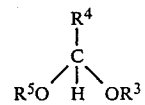  (III)

in which

R$^3$ and R$^4$ are defined as above, and

R$^5$ represents C$_1$-C$_{10}$-alkyl, unsubstituted phenyl or phenyl substituted by halogen, nitro or C$_1$-C$_4$-O-alkyl, in the presence of an catalyst of the formula

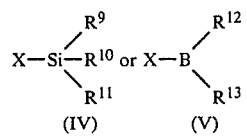

(IV)    (V)

in which $R^9$, $R^{10}$, $R^{11}$, $R^{12}$ and $R^{13}$ are identical or different and each represents $C_1$–$C_8$-alkyl, and X represents $FSO_3$, $CF_3CO_2$, $ClO_4$, $BF_4$, $CH_3SO_3$ or $CF_3(CF_2)_n$—$SO_3$ (in which n is 0, 1, 2, 3 or 4), in a suitable solvent.

2. A process according to claim 1, in which X represents $CF_3SO_3$.

3. A process according to any of claims 1 or 2, in which $R^6$, $R^7$, $R^8$, $R^9$, $R^{10}$, $R^{11}$, $R^{12}$ and $R^{13}$ denote methyl radicals.

4. A process according to claim 1, in which the reaction is carried out at a temperature between $-80°$ C. and $100°$ C.

5. A process according to claim 1, in which the solvent used is $CH_2Cl_2$, $CHCl_3$, acetonitrile, diethyl ether or tetrahydrofuran.

6. A process according to claim 1, in which the silyl compound of formula (II) is reacted with an equimolar amount or an excess of the acetal of formula (III).

7. A process according to claim 1, in which about 1/10 equivalent, relative to the silyl compound of formula (II) of the catalyst of formula (IV) or (V) is added.

8. A process for the production of 1-0-(1′-methoxy methyl)-2,3,4,6-tetra-0-acetyl-β-D-glucopyranose which comprises reacting a compound of the formula

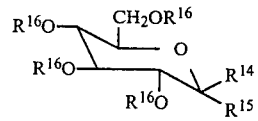

wherein
$R^{16}$ is acetyl, $R^{15}$ is H and
$R^{14}$ is O-Si($CH_3$)$_3$
with an acetal of the formula

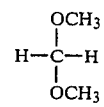

in the presence of trimethyl silyl trifluoromethane sulphonate as catalyst in a suitable solvent.

* * * * *